United States Patent [19]

Barbee et al.

[11] Patent Number: 5,573,623
[45] Date of Patent: Nov. 12, 1996

[54] APPARATUS FOR CONTACTLESS REAL-TIME IN-SITU MONITORING OF A CHEMICAL ETCHING PROCESS

[75] Inventors: Steven G. Barbee, Dover Plains; Tony F. Heinz, Chappaqua; Leping Li, Poughkeepsie; Eugene H. Ratzlaff, Hopewell Junction, all of N.Y.

[73] Assignee: International Business Machines Corporation, Armonk, N.Y.

[21] Appl. No.: 531,259

[22] Filed: Sep. 20, 1995

Related U.S. Application Data

[62] Division of Ser. No. 269,860, Jun. 30, 1994, Pat. No. 5,480,511.

[51] Int. Cl.[6] ............................................. G01N 27/00
[52] U.S. Cl. ................................................... 156/345
[58] Field of Search ........................... 156/345, 627.1; 216/86

[56] References Cited

U.S. PATENT DOCUMENTS

| | | | |
|---|---|---|---|
| 2,933,675 | 4/1960 | Hoelzle | 324/30 |
| 3,163,568 | 12/1964 | LeMieux | 156/17 |
| 3,292,077 | 12/1966 | Sloughter | 324/30 |
| 3,553,052 | 1/1972 | Jubb, Jr. | 156/345 |
| 3,806,798 | 4/1974 | Gross | 324/30 R |
| 3,874,959 | 4/1975 | Hoekstra et al. | 156/7 |
| 3,959,046 | 5/1976 | Bussmann et al. | 156/7 |
| 3,964,956 | 6/1976 | Snyder | 156/345 |
| 4,207,137 | 6/1980 | Tretola | 156/627 |
| 4,338,157 | 7/1982 | Kanda | 156/627 |
| 4,497,699 | 2/1985 | deWit et al. | 204/129.2 |
| 4,621,037 | 11/1986 | Kanda et al. | 430/307 |
| 4,755,442 | 7/1988 | Hasebe et al. | 430/30 |
| 4,767,496 | 8/1988 | Hieber | 156/627 |
| 4,793,895 | 12/1988 | Kaanta et al. | 156/627 |
| 4,954,212 | 9/1990 | Gabriel et al. | 156/627 |
| 4,969,973 | 11/1990 | Rinck et al. | 156/627 |
| 4,995,939 | 2/1991 | Ferenczi et al. | 156/627 |
| 5,071,508 | 12/1991 | Scheithauer et al. | 156/627 |
| 5,081,421 | 1/1992 | Miller et al. | 324/671 |
| 5,198,072 | 3/1993 | Gabriel | 156/627 |
| 5,338,390 | 8/1994 | Barbee et al. | 156/627 |

FOREIGN PATENT DOCUMENTS

| | | | |
|---|---|---|---|
| 55-46568 | 4/1980 | Japan | H01L 21/88 |
| 59-52838 | 3/1984 | Japan | 156/627 |
| 59-113626 | 6/1984 | Japan | 156/627 |
| 273634 | 3/1990 | Japan | 156/627 |
| 496346 | 3/1992 | Japan | H01L 21/66 |
| 8100646 | 3/1981 | WIPO | 156/627 |

OTHER PUBLICATIONS

Goubau, W. M., "Capacitive Etch Rate Monitor for Dielecric Etching", IBM Technical Disclosure Bulletin vol. 31, No. 1, Jun. 1988, pp. 448–449.

Liu et al., "Resistance/Capacitance Methods for Determining Oxide Etch End Point", IBM Technical Disclosure Bulletin vol. 16, No. 8, Jan. 1974, pp. 2706–2707.

Hoekstra, J. P., "Establishing End Point During Delineation Process", IBM Technical Disclosure Bulletin vol. 16, No. 6, Nov. 1973, pp. 1717–1720.

Bassous et al., "An In–Situ Etch Rate Monitor Controller", IBM Technical Disclosure Bulletin vol. 20, No. 3, Aug. 1977, pp. 1232–1234.

*Primary Examiner*—Thi Dang
*Attorney, Agent, or Firm*—Alison D. Mortinger

[57] ABSTRACT

A contactless method and apparatus for in-situ chemical etch monitoring of an etching process during etching of a workpiece with a wet chemical etchant are disclosed. The method comprises steps of providing at least two toroidal windings in the wet chemical etchant to be proximate to but not in contact with the workpiece; and monitoring an electrical characteristic between said at least two toroidal windings, wherein a prescribed change in the electrical characteristic is indicative of a prescribed condition of the etching process. Such a method and apparatus are particularly useful in a wet chemical etch station.

38 Claims, 4 Drawing Sheets

APPARATUS FOR CONTACTLESS REAL-TIME IN-SITU MONITORING OF A CHEMICAL ETCHING PROCESS

This is a Divisional Patent Application of U.S. patent application Ser. No. 08/269,860, filed on Jun. 30, 1994, now U.S. Pat. No. 5,480,512.

BACKGROUND OF THE INVENTION

1. Field of the Invention

This invention generally relates to a method and apparatus for monitoring the etching condition of a chemical etching process, and more particularly, to a contactless real-time in-situ method and apparatus foe the same.

2. Discussion of the Related Art

Etch progress and etch end points must be carefully monitored and controlled in order to end etching processes at a desired time. In semiconductor processing, inadequate or excess etching time can result in undesirable film patterning. For instance, for semiconductor devices having film layers or features in the micron and sub-micron range, an inadequate etch or an excess etch would result in the insufficient removal or the excess removal of a desired layer. Insufficient removal of a desired layer can result in an undesired electrical open or electrical short when the desired layer to be removed is an insulator or a conductor, respectively. Additionally, if the etch is in excess, undercutting or punch through can occur resulting in poorly defined film patterning or total lift-off. Inadequate or excess etching further leads to undesirable reliability problems in the subsequently fabricated semiconductor device. As a semiconductor wafer is extremely expensive due to many processing steps involved in the making thereof, the need to critically control the etching end point in an etching process is highly desirable.

An etch end point must be accurately predicted and/or detected to terminate etching abruptly. Etch rates, etch times, and etch end points are difficult to consistently predict due to lot-to-lot variations in film thickness and constitution, as well as etchant temperature, flow, and concentration variability. That is, an etch rate is dependent upon a number of factors, which include, etchant concentration, etchant temperature, film thickness, and the film characteristics. Precise and strict control of any of these factors can be very expensive to implement, for example, concentration control.

Some currently used etch rate end point determination techniques depend on indirect measurement and estimation techniques. Some etch monitoring techniques have relied on external measurements of film thickness followed by etch rate estimation and an extrapolated etch end point prediction. However, etch rates may vary due to batch-to-batch differences in the chemical and physical characteristics of the film or the etchant. These extrapolation methods are inadequate.

As an alternative to indirect measurements and estimation techniques, real-time in-situ monitoring is preferred. Some in-situ techniques monitor the etch rate of a reference thin film. This may require additional preparation of a monitor wafer containing the reference thin film or a suitable reference may be unavailable. Still other techniques require physical contact of electrical leads with the wafer being etched and electrical isolation of those leads and associated areas of the wafer from the etchant. This presents problems associated with contamination, contact reliability and reproducibility, and the physical constraints which affect ease of use in manufacturing or automation.

It would thus be desirable to provide a method and apparatus which provides non-contact, real-time, in-situ monitoring of an etching condition of a wafer being etched.

SUMMARY OF THE INVENTION

An object of the present invention is to overcome the problems in the art discussed above.

Another object of the present invention is to provide a robust non-contact method of monitoring the etching condition of a wafer being etched.

Yet another object of the present invention is to provide an accurate real-time, in-situ method and apparatus for monitoring an etching condition of a workpiece being etched.

According to the present invention, a contactless method for in-situ chemical etch monitoring of an etching process during etching of a workpiece with a wet chemical etchant, comprises the steps of: a) providing at least two toroidal windings disposed in the wet chemical etchant to be proximate to but not in contact with the workpiece, each of said at least two toroidal windings having a principal axis through a respective hollow center portion thereof, wherein one of said at least two toroidal windings comprises a generator winding and wherein another one of said at least two toroidal windings comprises a detector winding; and b) monitoring an electrical characteristic of the workpiece and the wet chemical etchant between said at least two toroidal windings, wherein a prescribed change in the electrical characteristic is indicative of a prescribed condition of the etching process.

In addition, according to the present invention, a contactless in-situ chemical etch monitor for providing an indication of a prescribed condition of an etching process during etching of a workpiece with a wet chemical etchant comprises at least two toroidal windings, wherein each toroidal winding has a principal axis through a respective hollow center portion thereof, and further wherein one of the at least two toroidal windings comprises a generator winding and wherein another of the at least two toroidal windings comprises a detector winding. A positioning means positions the at least two toroidal windings in the wet chemical etchant to be proximate to but not in contact with the workpiece. A monitoring means monitors an electrical characteristic of the workpiece and the wet chemical etchant between the at least two toroidal windings, wherein a prescribed change in the electrical characteristic is indicative of the prescribed condition of the etching process.

BRIEF DESCRIPTION OF THE DRAWINGS

The foregoing and other teachings and advantages of the present invention will become more apparent upon a detailed description of the best mode for carrying out the invention as rendered below. In the description to follow, reference will be made to the accompanying drawings in which like reference numerals are carried forward, and in which.

CROSS-REFERENCE TO COPENDING APPLICATIONS

Copending U.S. patent application Ser. No. 07/985,413, filed Dec. 4, 1992, entitled now U.S. Pat. No. 5,338,390, "Contactless Real-Time In-Situ Monitoring of a Chemical Etching Process," assigned to the assignee of the present invention (attorney docket FI9-92-152), the disclosure of which is hereby incorporated by reference into the present application, describes a related method and apparatus for the contactless, real-time, in-situ monitoring of a chemical etching process during etching of a wafer in a wet chemical etchant bath, wherein two conductive electrodes are proximate to but not in contact with the at least one wafer, and further wherein the two electrodes are positioned on opposite front/back sides of the wafer. Six copending U.S. Patent Applications, filed on even date herewith, entitled variously: "Minimizing Overetch During A Chemical Etching Process", "Real Time Measurement Of Etch Rate During A Chemical Etching Process", "Measuring Film Etching Uniformity During A Chemical Etching Process", "Contactless Real-Time In-Situ Monitoring Of A Chemical Etching Process", "Fixture For In-Situ Noncontact Monitoring Of Wet Chemical Etching With Passive Wafer Restraint", "Method And Apparatus For Contactless Real-Time In-Situ Monitoring Of A Chemical Etching Process", assigned to the assignee of the present invention Ser. Nos. 08/269,864, 08/269,862, 08/269,861, 08/269,863, 08/269,859, and 08/269,865, respectively), describe improvements to the method and apparatus for contactless, real-time, in-situ monitoring of chemical etching disclosed in the 07/985,413 application. The disclosure of the six aforesaid copending applications is also hereby incorporated by reference into the present application.

DETAILED DESCRIPTION OF THE PREFERRED EMBODIMENTS

Figure 1:
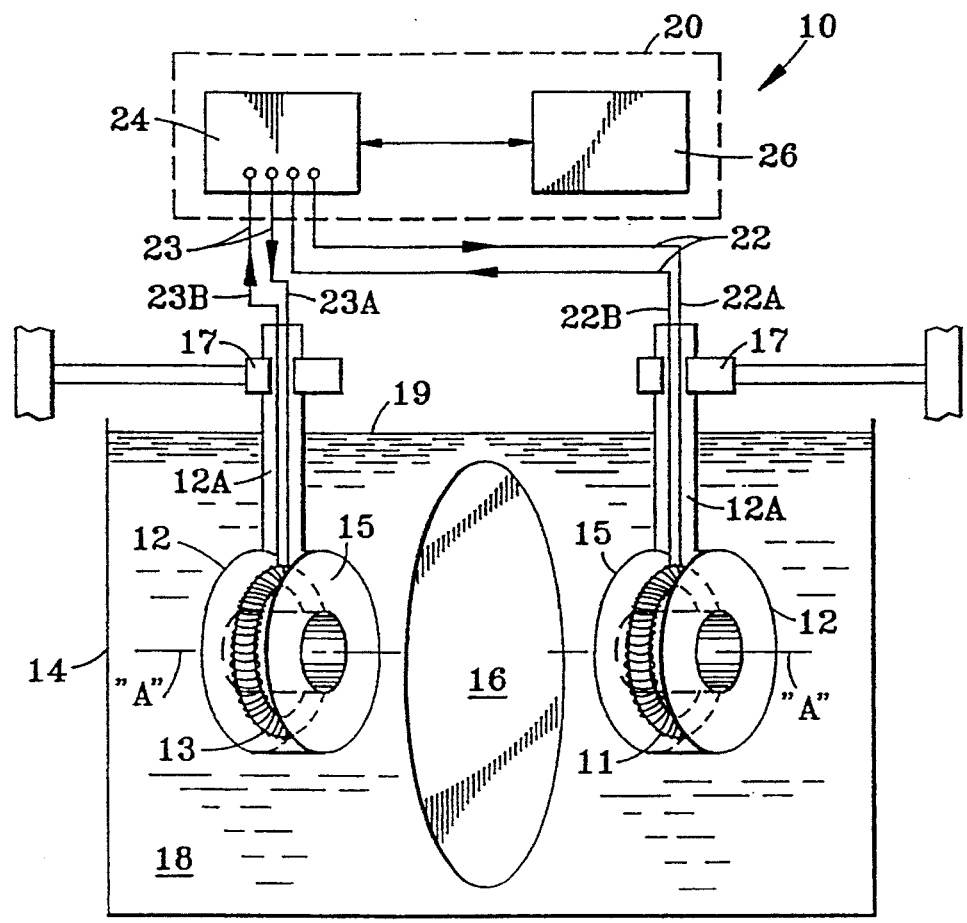
FIG. 1 shows a contactless real-time in-situ etching condition monitor according to the present invention.

Referring now to FIG. 1, there is shown a contactless real-time, in-situ monitor 10 for providing an indication of a prescribed condition in an etching process according to the present invention. Monitor 10 comprises at least two toroidal windings or toroids 12 positionable inside an etchant tank 14. One of the at least two toroidal windings 12 comprises a generator winding 11 and another of the at least two toroidal windings 12 comprises a detector winding 13, as will be further explained hereinbelow. Etchant tank 14 is of an appropriate size for receiving at least one workpiece or wafer 16 to be etched. Wafer 16 comprises, for example, a semiconductor wafer or substrate having at least one film layer thereon which is desired to be removed by a wet chemical etchant 18. The film layer may comprise a conducting, semiconducting, or dielectric film and further be patterned or unpatterned. The at least one wafer 16 is positioned in any suitable standard wafer carrier (not shown) and submerged in a bath of wet chemical etchant 18. The wet chemical etchant 18 comprises a suitable etchant for removing the desired film layer on the at least one wafer 16. While only one wafer is shown, more than one wafer may be placed in the etchant bath 18.

Each toroidal winding or toroid 12 can comprise, for example, any suitable commercially available toroidal winding encased in a dielectric material, such as available from Wayne Kerr of Woburn, Mass. or Omega Engineering Inc. of Stamford, Conn. Toroidal windings are known in the art and only briefly discussed herein. Each toroid 12 may comprise a toroid coil having an integral "arm" $12_A$ or rod of a prescribed shape and length. The prescribed shape and length of arm $12_A$ are selected to be such that a portion thereof integral with the toroidal coil can be submerged in the bath of wet chemical etchant 18 while another portion, suitable for clamping and positioning purposes, extends above and out of the bath of wet chemical etchant 18 during an etching process. Arm $12_A$ can comprise an arm perpendicular to the axis "A" of the toroidal opening or hollow center portion of the toroid. Arm $12_A$ and toroidal coil may further be assembled such that a dielectric material is coated or molded around the entire toroid assembly. The toroid arm $12_A$ is typically cylindrical, comprising a solid dielectric, through which electrical wires pass from the toroidal coil to external connections.

As indicated above, the toroidal winding is characterized by a principal axis "A" through a center bore or hollow center portion thereof. Referring to FIG. 1, toroids 11 and 13 can comprise, for example, respective toroidal windings encased in a suitable chemically inert dielectric material, such as polyvinyl ester, polypropylene, or Teflon. The casings of toroidal windings 12 further comprise a material which is insensitive to the bath of wet chemical etchant 18 and one which is noncontaminating. The casings of toroidal windings 11 and 13 further are relatively soft which advantageously obviates undesirable scratching or other damage to a wafer being etched in case of any inadvertent contact between the wafer and one or both of the toroids. The toroidal windings 11 and 13 are still further characterized by respective wire pairs 22 and 23 extending through a respective arm $12_1$, each wire pair comprising a lead wire and a return wire, $(22_a, 22_b)$ and $(23a, 23_b)$, respectively. Dimensions of the toroid casings may be on the order of one (1) inch inner diameter (I.D.) for the center bore, two and a half (2 ½) inches in depth, and three and a half (3 ½) inches outer diameter (O.D.). Toroid 11 serves as a generator toroid, while toroid 13 serves as a detector toroid. While specific dimensions of the toroidal windings are presented herein, it should be noted that toroidal windings having other dimensions and/or characteristics may be used so long as the above fundamental properties are maintained.

Toroidal windings 12 are distinguishable over the use of exposed electrodes as taught in copending U.S. patent application Ser. No. 07/985,413. The use of exposed electrodes presents several concerns as follows. One concern relates to contamination relating to dissolution of the electrode over a period of time, or its extended use. A second concern is that the electrode may potentially catalyze undesired reactions, e.g., Pt is a well known catalyst. Furthermore, electrodes may also lead to undesired electrochemical reactions, such as, electrolysis. These concerns are not present with the use of toroids as taught by the present invention.

Referring again to FIG. 1, toroidal windings 12 are positionable within the bath of wet chemical etchant 18 by any suitable means, such as adjustable positioning clamps 17. Respective adjustable positioning clamps 17 attach to respective toroidal arms $12_A$ of toroidal windings 11 and 13 for positioning the same in a desired location and orientation within the bath of wet chemical etchant 18. As shown in FIG. 1, the faces 15 of toroidal windings 12 are oriented perpendicular to the liquid surface 19 of bath 18 and further wherein toroidal windings 12 are substantially parallel such that their respective axes "A" are in alignment with one another. As further shown in FIG. 1, the toroidal windings 12 are positioned on opposite sides of the at least one wafer 16, wherein wafer 16 is in between the toroidal windings 12. Furthermore, toroidal windings 12 are spaced away from the at least one wafer 16 by a prescribed distance, for example, on the order of five (5) mm. The prescribed distance is established such that the toroidal windings 12 are remote from and not in direct contact with the at least one wafer 16, thus eliminating any need for special physical contacting electrodes or other contacting means, while permitting suitable etchant access and flow. Still further, toroidal windings 12 are positioned to be at an approximate vertical center of the bath of wet chemical etchant 18, further corresponding to an approximated vertical center of the at least one wafer 16 being etched. The remote and non-contact toroidal windings 12 preclude any physical damage to the at least one wafer 16. As indicated above, an advantage of using toroidal windings 12 is that the toroidal windings are encased in a relatively soft dielectric material (such as Teflon) which obviates undesirable scratching or damaging of the wafer thereby in case of any inadvertent contact therebetween.

Toroidal windings 11 and 13 are connected to an electrical characteristic monitoring device 20 by electrical wire pairs 22 and 23, respectively. Electrical wire pairs 22 and 23 comprise suitable wire pairs. Wire pairs 22 and 23 are further sheathed with chemically inert dielectric insulating material (not shown) as necessary.

Electrical characteristic monitoring device 20 can comprise, for example, an impedance analyzer 24 and a data recording and displaying device 26, such as any suitable commercially available LCR impedance analyzer, and chart recorder, respectively. It should be noted that electrical characteristic monitoring device 20 can likewise comprise an impedance analyzer and a computer or a programmable controller, the computer or programmable controller additionally providing feedback control to initiate, control, and terminate an etching operation. For instance, the computer or programmable controller can be connected to a robotic arm (not shown), the computer for appropriately controlling the robotic arm in response to an output of the electrical characteristic monitoring means 20 for the robotic arm to raise and lower a wafer carrier containing the at least one wafer 16 into and out of the wet chemical etchant 18 according to the requirements of the etching process. Furthermore, impedance analyzer 24 may likewise comprise a suitable AC waveform generator or oscillator and lock-in amplifier. Impedance analyzers, waveform generators, lock-in amplifiers, computers, and programmable controllers are well known in the art.

In operation, the present invention provides a real-time method and apparatus for monitoring a prescribed etching characteristic, such as, etch rate or etch end point of an etching process. Etch end point is used herein to refer to the point in time when a desired film layer or portion thereof is completely removed. Monitoring of the prescribed etching characteristic is effected by electrically sensing, in-situ, changes in an electrical characteristic, such as, the impedance or an element or elements of impedance (e.g., reactance and/or resistance), between the two toroidal windings 12. The toroidal windings 12 are positioned proximate to but not in contact with the etched wafer 16. During the removal of a conducting, semiconducting, or dielectric film from the etched wafer 16, the impedance of the etched wafer 16 and its environment changes. The changes of impedance with time are related to etching rates. Changes in the rate of change in the impedance element(s), specifically slope reversals and trend discontinuities, are related to changes in phase transitions where a change in the etchant-wafer interface has occurred. These impedance transitions mark distinct etching characteristics, such as, etch end points. Thus etching rates and etching end points can be readily determined in real-time.

The contactless real-time, in-situ chemical etching method and apparatus of the present invention operate by first placing the wafer 16 to be etched into the bath of wet chemical etchant 18. Wafer 16 is proximate to but not touching toroidal windings 12, thus avoiding an unnecessary and potentially damaging contact between the wafer 16 and toroidal windings 12. During removal of a desired film or films from wafer 16, the impedance of the etched wafer 16 and its environment changes. An alternating electrical field is generated through toroidal winding 11 and changes in a field-induced current are detected and measured through toroidal winding 13, wherein such changes are a result of the effect of the changing impedance of the wafer 16 and its environment during etching. In particular, toroidal winding 11 is used to create a sinusoidally modulated electrical field. An appropriate modulation signal is provided to toroidal winding 11 from impedance analyzer 24 on wire pair 22 for creation of the modulated electrical field. The modulation signal may comprise for example a signal on the order of one (1) volt at ten (10) KHz. Toroidal winding 13 serves as a detector winding or current sensor. Toroidal windings 12 are thus used for measuring an impedance such that wafer 16 is subjected to an electric field developed by one toroidal winding and sensed by the other toroidal winding. The impedance characteristic of wafer 16 being etched and its environment is measured in a standard way for measuring impedance, and more particularly in the present instance, by applying an appropriate AC or pulsed, current or voltage signal to the toroidal winding 11 and monitoring the passed current or developed potential via toroidal winding 13. This is readily accomplished via impedance analyzer 24 of electrical characteristic monitoring means 20. Electrical characteristic monitoring means 20 provides a means for monitoring the passed current or developed potential sensed via toroidal winding 13 in an appropriate way. That is, monitoring means 20 measures the magnitude and phase of the electrical signal induced in the detector toroidal winding 13.

Described in another way, the present invention provides for the in-situ monitoring of dimensional changes of the wafer in the liquid etchant. Dimensional changes, such as film thinning, are monitored by sensing resultant changes in the electrical characteristics of the wafer and the etchant environment. The at least two toroidal windings 12 are proximate to but not in direct physical contact with the at least one wafer 16. The toroidal windings 12 and wafer 16 are in ohmic or capacitive contact with the wet chemical etchant 18. Electrical characteristic monitoring means 20 provides a means of monitoring changes in impedance or changes in an appropriate element of the impedance between the electrodes.

EXAMPLE

Operation of the present invention will now be further described using an example. The present invention has been applied to the monitoring of the etching of a blanket aluminum oxide from a silicon wafer 16 in an etchant bath of dilute (approximately 1%) aqueous hydrofluoric (HF) acid etchant 18. The present invention provided sufficient information to accurately establish an etch end point, to include where the etchant had just penetrated and also removed the oxide layer. The etching process was conducted in a small square tub measuring approximately 8 inches by 10 inches wide by 7 inches deep, filled with about 6 inches of dilute HF etchant. All measurements were made at ambient room temperature and no thermostatting was used.

A Teflon wafer carrier (not shown) was then placed in the center of the tub, wafer carriers being well known in the art. Two toroidal windings 11 and 13 encased in polyvinyl ester were then placed inside the carrier so that the center holes thereof were axially aligned such that the axis "A" was perpendicular to the wafer plane. The toroid central axis was positioned near the central rotational axis of symmetry of the wafer. The toroid casings were positioned to be distanced about 5 mm from the wafer. Toroid 11 served as a field generator, while the other toroid 13 was used as a detector. Field generation and detection was implemented via electrical characteristic monitoring means 20.

Figure 2:
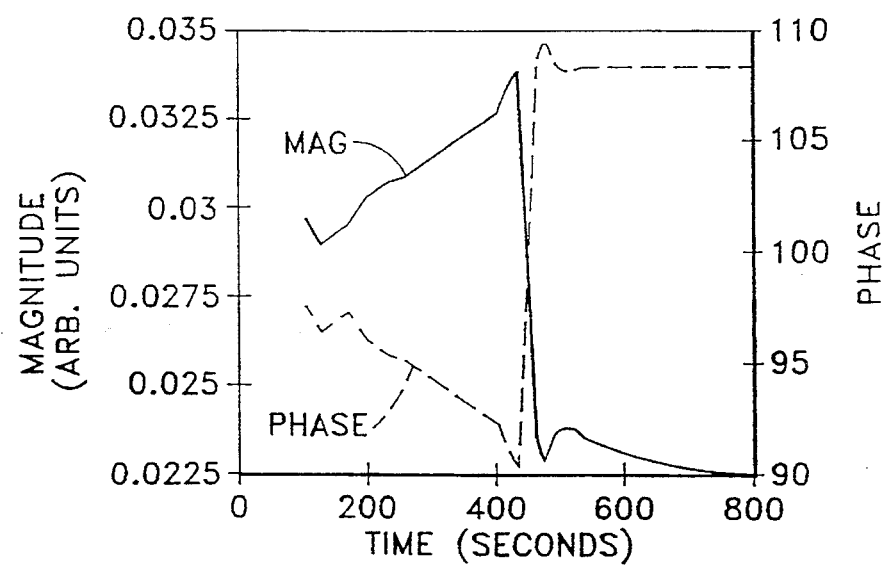
FIG. 2 shows a graph of monitored electrical characteristics of etching of a film on a substrate using the present invention shown in FIG. 1.

A silicon wafer, with a blanket aluminum oxide thin film of about 1000 Angstroms thick thereon, was thereafter placed between the toroids 11 and 13 and etched. The magnitude and phase of the detected signal was monitored and recorded during the etch. The recorded results are shown in FIG. 2. Abrupt changes after about 450 seconds of etching correlate to an etch end point. That is, a prescribed change in the electrical characteristic is indicative of a prescribed condition of the etching process.

As can be seen from the above example, the method of the present invention provides a reliable end point detection with good signal to noise (S/N) ratio. Other material combinations such as semiconductor or insulator on conductor or conductor on insulator should work equally well with the present invention.

The present invention thus advantageously provides sufficient information to accurately identify etching conditions of an etching process, and more particularly, an etching end point wherein the etchant has removed a desired film layer.

Figure 3:
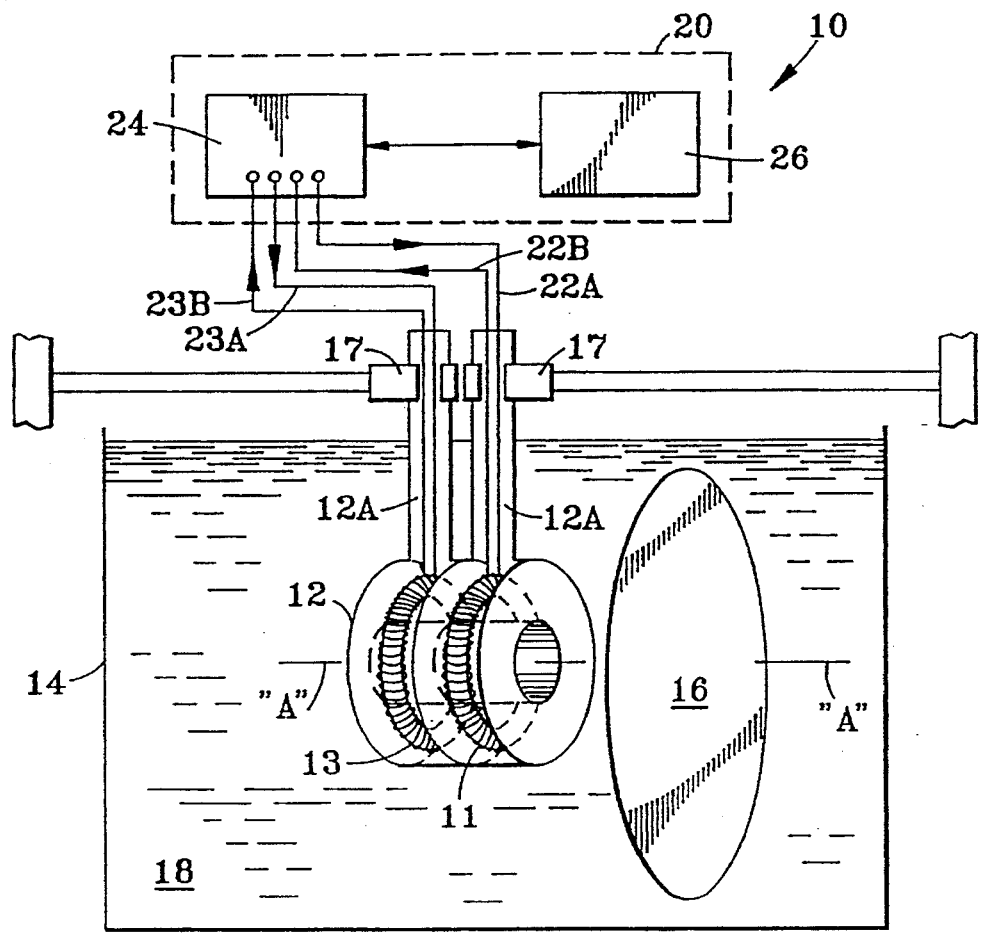
FIG. 3 shows a contactless real-time in-situ etching condition monitor according to an alternate embodiment of the present invention.
Figure 4:
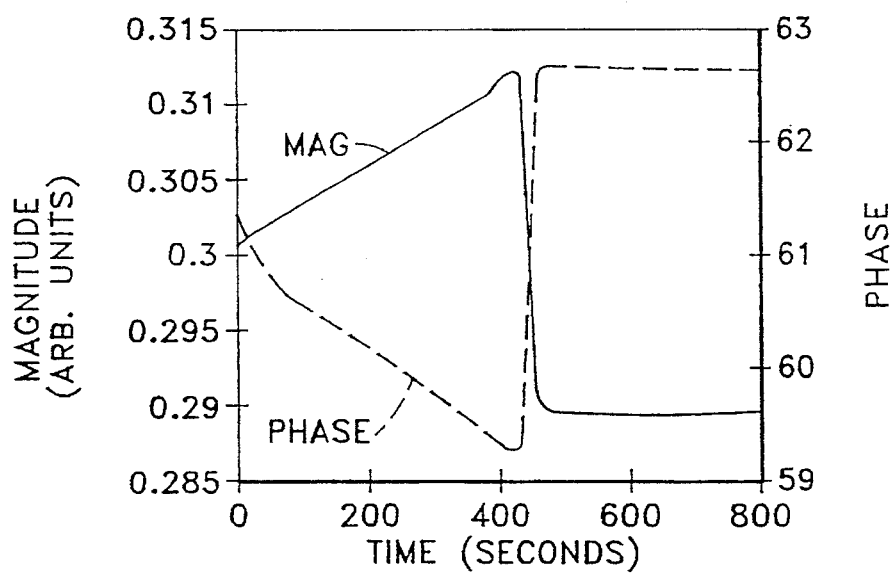
FIG. 4 shows a graph of monitored electrical characteristics of etching of a film on a substrate using the present invention shown in FIG. 3.

Referring now to FIG. 3, an alternate embodiment of the present invention is shown. The alternate embodiment is substantially the same as the preferred embodiment, with the following differences. Toroidal windings 11 and 13 are positioned on a same side of the wafer 16 during the etching process. Furthermore, the toroidal windings 11 and 13 are in axial alignment with each other. While it is shown that windings 11 and 13 are separately packaged, windings 11 and 13 may also be integrally packaged. An etching process was carried out, similar to that discussed above with respect to the preferred embodiment, using the embodiment shown in FIG. 3 for the etching of a blanket aluminum oxide from a silicon wafer in dilute HF. The results shown in FIG. 4 were obtained.

Figure 5:
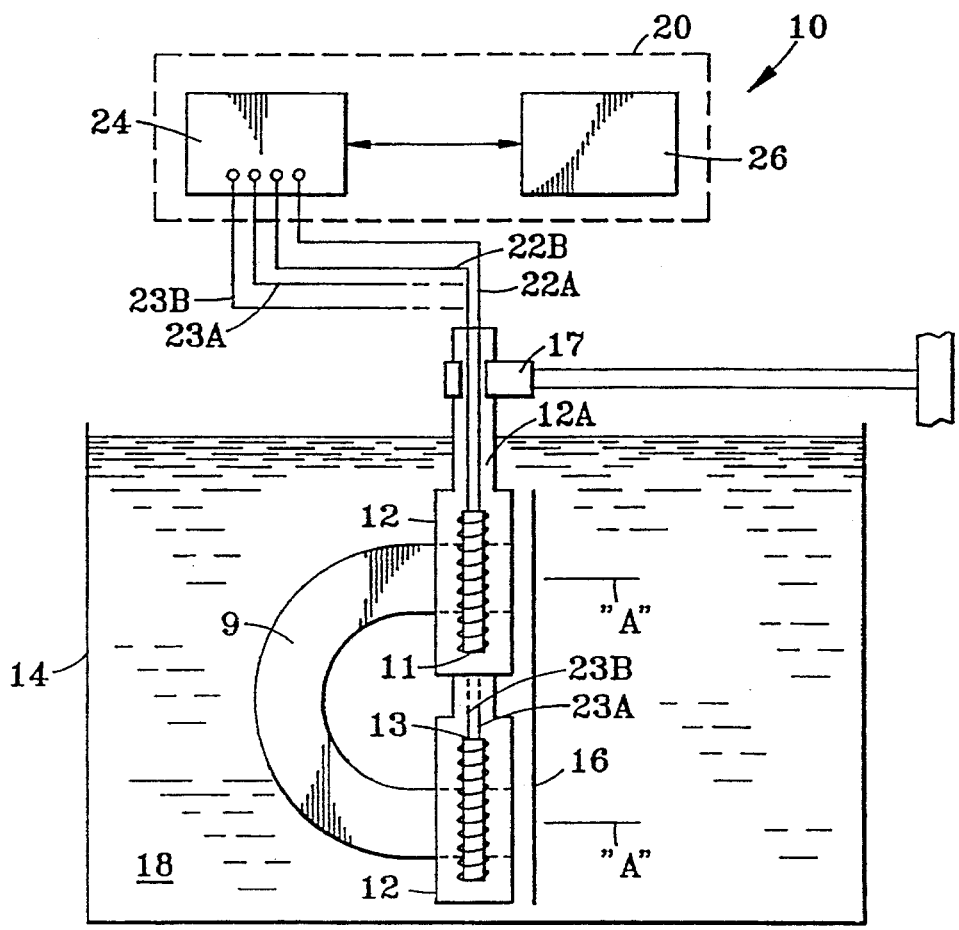
FIG. 5 shows a contactless real-time in-situ etching condition monitor according to yet another alternate embodiment of the present invention.
Figure 6:
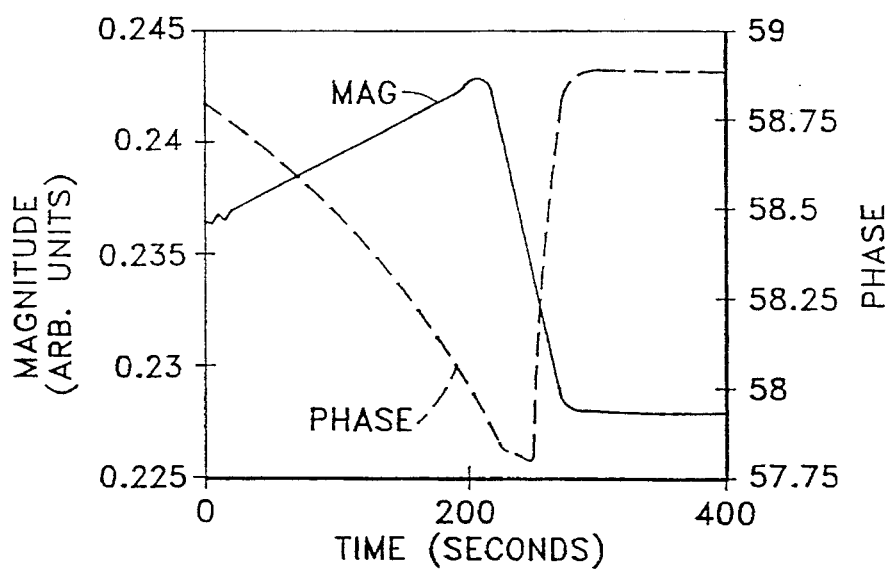
FIG. 6 shows a graph of monitored electrical characteristics of etching of a film on a substrate using the present invention shown in FIG. 5.

Referring now to FIG. 5, yet another alternate embodiment of the present invention is shown. The alternate embodiment is substantially the same as the preferred embodiment, with the following differences. Toroidal windings 11 and 13 are positioned on a same side of the wafer 16 during the etching process. Furthermore, the toroidal windings 11 and 13 are positioned such that the respective axes thereof are parallel with each other. Furthermore, a conduit or piping member 9 provides a means for channeling a current-carrying volume of etchant between the toroidal windings 11 and 13. The conduit 9, preferably comprising a chemically inert dielectric material, is connected between the hollow center portion of toroidal winding 11 and the respective hollow center portion of toroidal winding 13. Conduit 9 advantageously channels electrical field currents through both toroidal windings 11 and 13. Such channeling advantageously increases measurement sensitivity. An etching process was carried out, similar to that discussed above with respect to the preferred embodiment, using the embodiment shown in FIG. 5 for the etching of a blanket aluminum oxide from a silicon wafer in dilute HF. The results shown in FIG. 6 were obtained.

Figure 7:
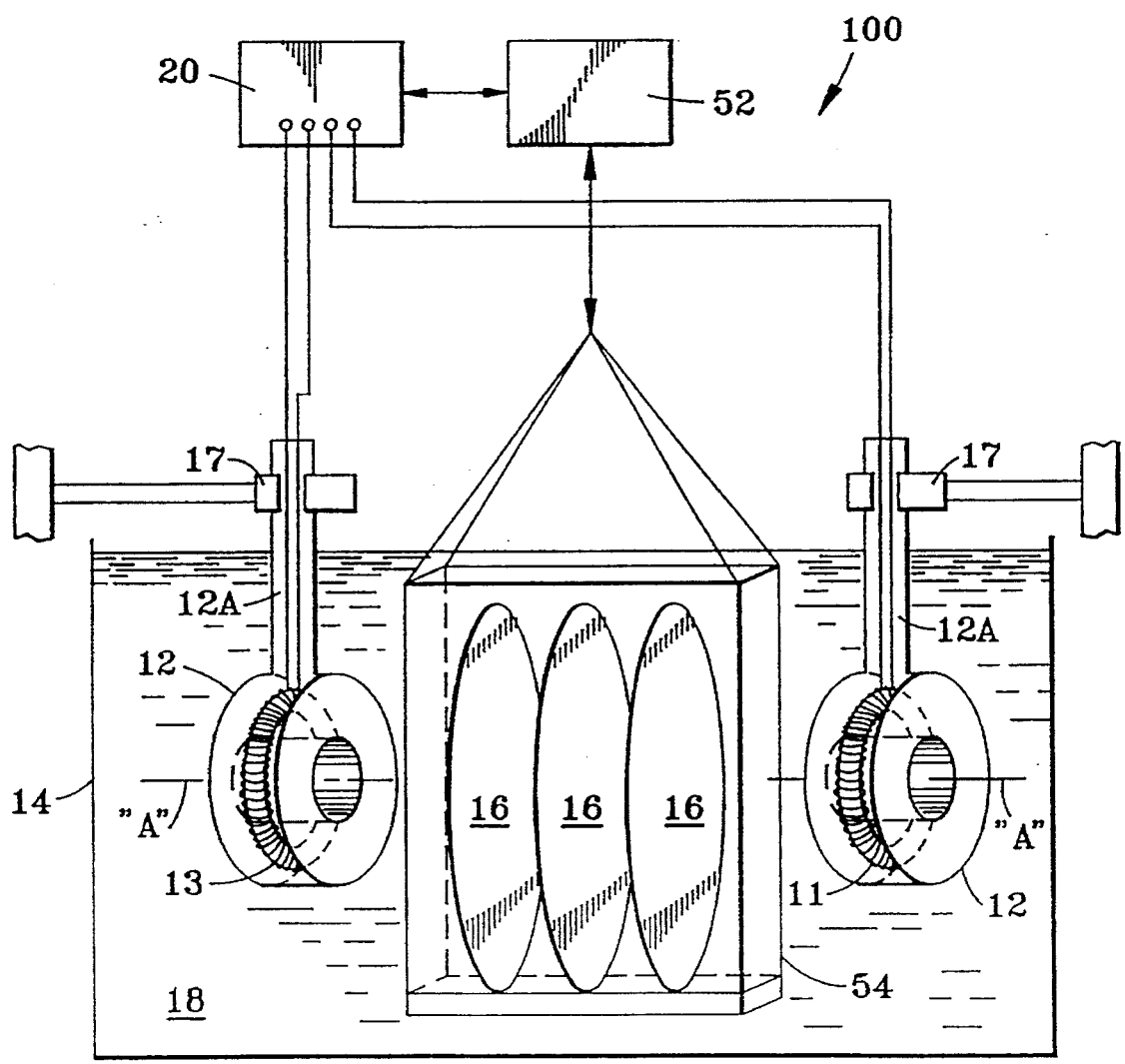
FIG. 7 shows an etch station according to the present invention.

Referring now to FIG. 7, in an alternate embodiment of the present invention, an etch station 100 incorporating the contactless real-time in-situ monitor 10 further includes a control means 52. Control means 52 is responsive to electrical characteristic monitoring means 20. Control means 52 can comprise, for example, a computer or programmable controller as discussed above, in conjunction with any suitable mechanism, such as a robotic arm (not shown) and a wafer carrier 54, for raising and lowering the wafer 16 into and out of the bath of wet chemical etchant 18. Means 52 thus controls the placement of wafer 16 into and out of the bath of wet chemical etchant 18 in response to the sensing of a prescribed etching condition or conditions by the electrical characteristic monitoring means 20. Means 52 may likewise control the flow of etchant 18 into or out of etchant tank 14 in response to the sensing of a prescribed etching condition or conditions by the electrical characteristic monitoring means 20. Thus, etch station 100 provides accurate and highly efficient etching control.

Thus there has been shown a real-time in-situ monitoring method and apparatus which provide accurate, non-contact, monitoring of an etching characteristic of an etching process. Such a method and apparatus are inexpensive to implement and ensure the integrity of the etched wafer or wafers. Etching of a wafer can be controlled precisely.

While the invention has been particularly shown and described with reference to the preferred embodiment thereof, it will be understood by those skilled in the art that various changes in form and detail may be made therein without departing from the spirit and scope of the invention. For example, system condition parameters, such as impedance analyzer frequency, etc., may be adjusted accordingly to obtain optimum detection sensitivity. Also, a component described as comprising a dielectric material may also likewise comprise an alternate material coated with a chemically inert dielectric material.

What is claimed is:

1. A contactless in-situ chemical etch monitor for providing an indication of a prescribed condition of an etching process during etching of a workpiece with a wet chemical etchant, said monitor comprising:

a) at least two toroidal windings, wherein each toroidal winding has a principal axis through a respective hollow center portion thereof, and further wherein one of said at least two toroidal windings comprises a generator winding and wherein another of said at least two toroidal windings comprises a detector winding;

b) means for positioning said at least two toroidal windings in the wet chemical etchant to be proximate to but not in contact with the workpiece; and c) means for monitoring an electrical characteristic of the workpiece and the wet chemical etchant between said at least two toroidal windings, wherein a prescribed change in the electrical characteristic is indicative of the prescribed condition of the etching process.

2. The monitor of claim 1, wherein said at least two toroidal windings comprise two toroidal windings.

3. The monitor of claim 2, wherein said positioning means further positions the two toroidal windings to be disposed one each on opposite sides of the workpiece, and further wherein the two toroidal windings are in axial alignment with each other.

4. The monitor of claim 2, wherein said positioning means further positions the two toroidal windings to be disposed on a same side of the workpiece, and further wherein the two toroidal windings are in axial alignment with each other.

5. The monitor of claim 2, wherein said positioning means further positions the two toroidal windings to be disposed on a same side of the workpiece, and further wherein the two toroidal windings are positioned such that respective axes of the two toroidal windings are parallel with each other.

6. The monitor of claim 5, further comprising d) means for directing a current-carrying volume between the two toroidal windings.

7. The monitor of claim 6, wherein said directing means comprises a conduit connected between the center hollow portions of the two toroidal windings.

8. The monitor of claim 7, wherein said directing means further comprises a chemically inert dielectric material coated upon the two toroidal windings and the conduit.

9. The monitor of claim 1, wherein said monitoring means comprises an impedance monitor and further wherein the prescribed change comprises a prescribed change in impedance.

10. The monitor of claim 9, wherein said at least two toroidal windings comprise two toroidal windings.

11. The monitor of claim 10, wherein said positioning means further positions the two toroidal windings to be disposed one each on opposite sides of the workpiece, and further wherein the two toroidal windings are in axial alignment with each other.

12. The monitor of claim 10, wherein said positioning means further positions the two toroidal windings to be disposed on a same side of the workpiece, and further wherein the two toroidal windings are in axial alignment with each other.

13. The monitor of claim 10, wherein said positioning means further positions the two toroidal windings to be disposed on a same side of the workpiece, and further wherein the two toroidal windings are positioned such that respective axes of the two toroidal windings are parallel with each other.

14. The monitor of claim 13, further comprising d) means for directing a current-carrying volume between the two toroidal windings.

15. The monitor of claim 14, wherein said directing means comprises a conduit connected between the center hollow portions of the two toroidal windings.

16. The monitor of claim 15, wherein said directing means further comprises a chemically inert dielectric material coated upon the two toroidal windings and the conduit.

17. The monitor of claim 1, further comprising d) means for directing a current-carrying volume between said at least two toroidal windings.

18. The monitor of claim 17, wherein said directing means comprises a conduit connected between the center hollow portions of said at least two toroidal windings.

19. The monitor of claim 18, wherein said directing means further comprises a chemically inert dielectric material coated upon said at least two toroidal windings and said conduit.

20. An etch station having contactless in-situ control of an etching process during etching of a workpiece with a wet chemical etchant, said etch station comprising:

a) at least two toroidal windings, wherein each toroidal winding has a principal axis through a respective hollow center portion thereof, and further wherein one of said at least two toroidal windings comprises a generator winding and wherein another of said at least two toroidal windings comprises a detector winding;

b) means for positioning said at least two toroidal windings in the wet chemical etchant to be proximate to but not in contact with the workpiece; and c) means for monitoring an electrical characteristic of the workpiece and the wet chemical etchant between said at least two toroidal windings, wherein a prescribed change in the electrical characteristic is indicative of the prescribed condition of the etching process.

21. The etch station of claim 20, wherein said at least two toroidal windings comprise two toroidal windings.

22. The etch station of claim 21, wherein said positioning means further positions the two toroidal windings to be disposed one each on opposite sides of the workpiece, and further wherein the two toroidal windings are in axial alignment with each other.

23. The etch station of claim 21, wherein said positioning means further positions the two toroidal windings to be disposed on a same side of the workpiece, and further wherein the two toroidal windings are in axial alignment with each other.

24. The etch station of claim 21, wherein said positioning means further positions the two toroidal windings to be disposed on a same side of the workpiece, and further wherein the two toroidal windings are positioned such that respective axes of the two toroidal windings are parallel with each other.

25. The etch station of claim 24, further comprising d) means for directing a current-carrying volume between the two toroidal windings.

26. The etch station of claim 25, wherein said directing means comprises a conduit connected between the center hollow portions of the two toroidal windings.

27. The etch station of claim 26, wherein said directing means further comprises a chemically inert dielectric material coated upon the two toroidal windings and the conduit.

28. The etch station of claim 20, wherein said monitoring means comprises an impedance monitor and further wherein the prescribed change comprises a prescribed change in impedance.

29. The etch station of claim 28, wherein said at least two toroidal windings comprise two toroidal windings.

30. The etch station of claim 29, wherein said positioning means further positions the two toroidal windings to be disposed one each on opposite sides of the workpiece, and further wherein the two toroidal windings are in axial alignment with each other.

31. The etch station of claim 29, wherein said positioning means further positions the two toroidal windings to be disposed on a same side of the workpiece, and further wherein the two toroidal windings are in axial alignment with each other.

32. The etch station of claim 29, wherein said positioning means further positions the two toroidal windings to be disposed on a same side of the workpiece, and further wherein the two toroidal windings are positioned such that respective axes of the two toroidal windings are parallel with each other.

33. The etch station of claim 32, further comprising d) means for directing a current-carrying volume between the two toroidal windings.

34. The etch station of claim 33, wherein said directing means comprises a conduit connected between the center hollow portions of the two toroidal windings.

35. The etch station of claim 34, wherein said directing means further comprises a chemically inert dielectric material coated upon the two toroidal windings and the conduit.

36. The etch station of claim 20, further comprising
d) means for directing a current-carrying volume between said at least two toroidal windings.

37. The etch station of claim 36, wherein said directing means comprises a conduit connected between the center hollow portions of said at least two toroidal windings.

38. The etch station of claim 37, wherein said directing means further comprises a chemically inert dielectric material coated upon said at least two toroidal windings and said conduit.

* * * * *